US012670624B1

(12) United States Patent
James, Jr.

(10) Patent No.: US 12,670,624 B1
(45) Date of Patent: **\*Jun. 30, 2026**

(54) SYSTEM FOR PRODUCING CONSISTENT MEDICAL IMAGE DATA THAT IS VERIFIABLY CORRECT

(71) Applicant: TRUE-See Systems, LLC, New Orleans, LA (US)

(72) Inventor: Francis Godwin James, Jr., New Orleans, LA (US)

( * ) Notice: Subject to any disclaimer, the term of this patent is extended or adjusted under 35 U.S.C. 154(b) by 141 days.

This patent is subject to a terminal disclaimer.

(21) Appl. No.: 18/599,526

(22) Filed: Mar. 8, 2024

Related U.S. Application Data

(63) Continuation of application No. 17/185,939, filed on Feb. 25, 2021, now Pat. No. 11,961,260, which is a continuation-in-part of application No. 14/209,557, filed on Mar. 13, 2014, now Pat. No. 10,973,412.

(60) Provisional application No. 61/799,843, filed on Mar. 15, 2013.

(51) Int. Cl.
| | |
|---|---|
| *G06T 7/90* | (2017.01) |
| *G06K 7/14* | (2006.01) |
| *G06T 7/00* | (2017.01) |
| *G06T 7/80* | (2017.01) |
| *G06T 17/00* | (2006.01) |
| *G06T 19/20* | (2011.01) |
| *G16H 10/60* | (2018.01) |
| *G16H 30/20* | (2018.01) |
| *H04N 9/64* | (2023.01) |
| *H04N 23/67* | (2023.01) |

(52) U.S. Cl.
CPC .............. *G06T 7/90* (2017.01); *G06K 7/1413* (2013.01); *G06T 7/0016* (2013.01); *G06T 7/80* (2017.01); *G06T 17/00* (2013.01); *G06T 19/20* (2013.01); *G16H 10/60* (2018.01); *G16H 30/20* (2018.01); *H04N 9/646* (2013.01); *H04N 23/67* (2023.01); *G06T 2200/04* (2013.01); *G06T 2200/24* (2013.01); *G06T 2207/10028* (2013.01); *G06T 2207/30168* (2013.01); *G06T 2210/41* (2013.01); *G06T 2219/2012* (2013.01)

(58) Field of Classification Search
CPC .. G06T 7/90; G06T 7/80; G06T 17/00; G06T 19/20; G06T 7/0016; G06T 2200/04; G06T 2200/24; G06T 2207/10028; G06T 2210/41; G06T 1/0021; G06T 2207/30168; G06K 7/1413; G16H 10/60; G16H 30/20; H04N 9/646; H04N 23/67
See application file for complete search history.

(56) References Cited

U.S. PATENT DOCUMENTS

| | | | |
|---|---|---|---|
| 2007/0242877 A1* | 10/2007 | Peters .................... G06V 10/75 382/167 |
| 2011/0117025 A1* | 5/2011 | Dacosta ............. G01N 21/6486 435/5 |

\* cited by examiner

*Primary Examiner* — Sing-Wai Wu

(57) ABSTRACT

A system produces medical images that are calibrated using a calibration slate. A subject is photographed with a calibration slate shown in the image. The calibration slate includes printed colors. The printed colors shown in the captured image can be compared against standard colors associated with the slate to color calibrate the image. Various types of medical images such as images showing wounds or other skin conditions may be color calibrated using the system.

31 Claims, 11 Drawing Sheets

10

10

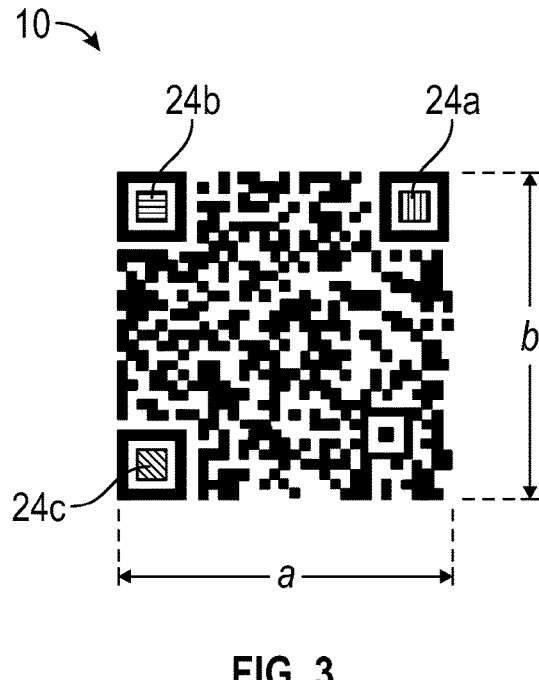
FIG. 3
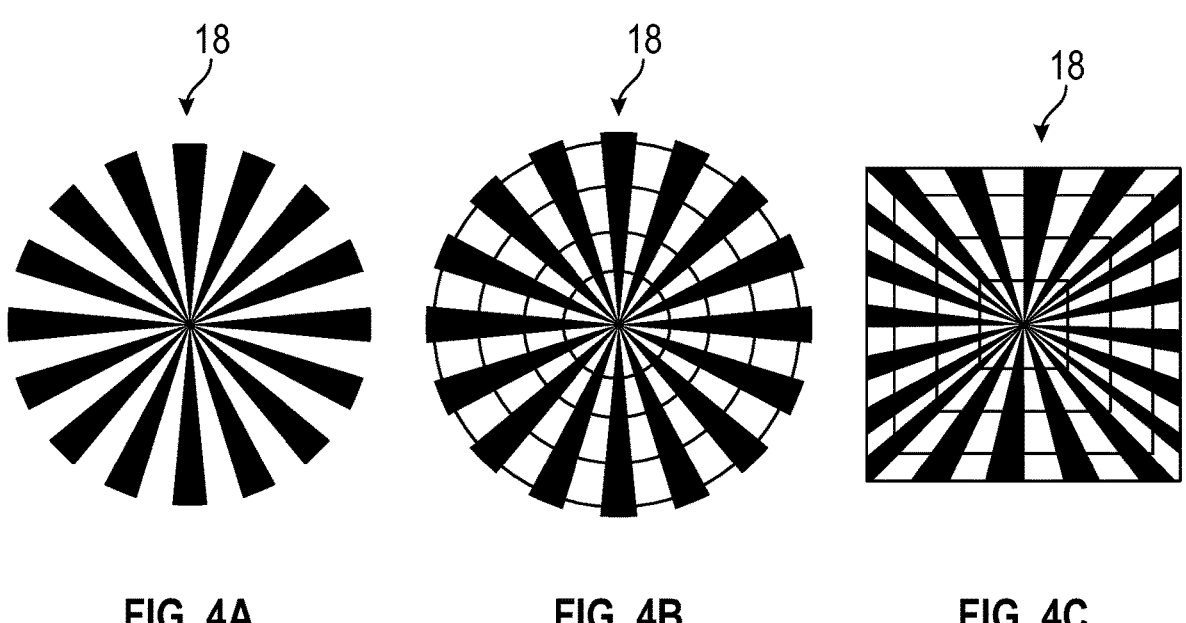
FIG. 4A          FIG. 4B          FIG. 4C

10

10

10

10

SYSTEM FOR PRODUCING CONSISTENT MEDICAL IMAGE DATA THAT IS VERIFIABLY CORRECT

CROSS REFERENCES

This application is a continuation of U.S. application Ser. No. 17/185,939, filed on Feb. 25, 2021, which is a continuation-in-part of U.S. application Ser. No. 14/209,557, filed on Mar. 13, 2014, which claims the benefit of U.S. Provisional Application No. 61/799,843, filed on Mar. 15, 2013, which applications are incorporated herein by reference in their entirety.

FIELD OF THE DISCLOSURE

The subject matter of the present disclosure refers generally to a system and method of producing medical images using a calibration slate. The system and method provide consistently accurate color calibrated visual representations of medical subjects such as wounds or skin conditions.

BACKGROUND

Photo-documentation is widely used in the medical field to create a visual record of patient wounds and skin conditions. Medical photo-documentation is a critical aspect of the medical record for wounds and skin conditions because such documentation provides a visual component to the medical record to support a written diagnosis and course of care. Thus, in medical photo-documentation, the accuracy of the color of visual representations is important as such representations may be critical to diagnosis and treatment of wounds or skin conditions, as well for assessment of the efficacy of a rendered course of treatment and for medical reimbursement purposes. However, the color consistency and accuracy of color photographs used in the medical field may vary significantly due to a variety of factors, such as the type of device used to capture a specific photograph, the lighting that illuminates the subject of the photograph, and differences in camera settings, among other factors. In addition, most, if not all, current visual recording devices utilize software to adjust and manipulate the color of an image without reference to a known color or photographic standard by which to judge the accuracy of the color of the photograph. Further, the colors of a captured image may be automatically manipulated by camera software without any means of verifying that color manipulation has or has not occurred. These factors may cause the visual medical record of a patient to be not only inaccurate but also unverifiable. If any of these factors cause the medical record to inaccurately represent the medical subject, diagnosis and/or evaluation of the patient may be adversely affected.

In addition to accurate color representation, diagnosis and/or evaluation of a patient, particularly of patient wounds, also requires an accurate depiction of the depth of a wound and how the depth or contours of the wound change over time during the healing process. Different portions of wounds, particularly severe wounds covering substantial portions of the patient's body, may heal at different rates, during which time the depth of the wound may change. Thus, to provide a full indication of the condition of a wound at any given time, medical professionals must have an accurate depiction of both the color of all parts of the wound as well as the depth and contours of the wound. In addition, it is important for medical professionals to understand how the depth of a wound has changed to fully evaluate the healing process. However, typical photo-documentation of patient wounds does not generally provide an accurate representation of the contours of wounds and how those contours change during the healing process, thereby providing an incomplete picture to medical professionals of how patient wounds develop.

Accordingly, a need exists in the art for a system and method of providing an accurate representation of a wound or skin condition of a patient, including both the color and the contours of the wound or skin condition. Furthermore, a need exists in the art for a system and method of providing a consistently accurate visual representation, including both color and contour, of how a patient wound or skin condition changes over a period of time.

SUMMARY

A system and method of producing medical image data that provides consistently accurate visual representations of three-dimensional medical images of patient wounds or skin conditions are provided. In one aspect, a method of color calibrating three-dimensional images related to the medical field is provided. The method comprises capturing one or more two-dimensional images of a subject on an image recording device and then producing a color calibrated three-dimensional image of the same subject. Each two-dimensional image, as well as the three-dimensional image, includes a calibration slate appearing in the image, which in each image is the same calibration slate. The calibration slate is positioned adjacent to the subject and may be attached directly to the subject of the images, and may preferably include an adhesive strip on the back of the calibration slate for attaching the slate to the subject. The calibration slate includes a print run number that identifies a batch of printed calibration slates, which includes the calibration slate appearing in the image. The calibration slate also includes a unique identifier that individually identifies the particular calibration slate appearing in the image. The calibration slate has a color chart comprising at least one color, and preferably a set of colors, for color calibrating each image.

In a preferred embodiment, to produce the three-dimensional image of the subject, the method includes generating point cloud data relating to the subject of each of the two-dimensional images. A three-dimensional model of the subject may then be constructed utilizing the point cloud data. One or more two-dimensional images may then be applied to the three-dimensional model to produce the three-dimensional image of the subject, which also shows the calibration slate that appears in each two-dimensional image. Alternatively, other suitable methods of producing a three-dimensional image may be utilized. For instance, the three-dimensional image may be constructed utilizing a plurality of two-dimensional images of the subject, which may be captured from varying angles relative to the subject, each including the same calibration slate in the image. To correct skew when capturing two-dimensional images of the subject from varying angles, the scale of objects relating to the subject and appearing in each of the two-dimensional images may be determined based on known measurements of one or more objects printed on the calibration slate that appears in each of the two-dimensional images.

To color calibrate the three-dimensional image, the system may measure numeric color values from one or more colors in the color chart printed on the calibration slate that appears in each image to be calibrated. Thus, because the calibration slate appears within the image, color values are measured from the captured image itself when measuring the color values from the calibration slate. The system may then read the print run number on the calibration slate and associate the print run number with a batch of printed calibration slates that includes the specific calibration slate appearing in the image. Because each calibration slate in the batch, including the slate appearing in the image, is substantially similar, the measured numeric color values have corresponding known numeric color values associated with the batch of calibration slates. The measured numeric color values may then be compared to the corresponding known numeric color values. Based on this comparison, the system may calculate a variance between the numeric color values measured from the image to be calibrated and the corresponding known numeric color values. The system may then calculate a calibration factor based on the variance. Once a calibration factor has been determined, the three-dimensional image may be color calibrated based on the calibration factor. In a preferred embodiment, to calibrate the three-dimensional image, each two-dimensional image is individually calibrated by adjusting the colors of each respective two-dimensional image by applying the calibration factor to numeric color values measured from each of the two-dimensional images. Alternatively, the three-dimensional image may be calibrated directly by adjusting the colors of the three-dimensional image by applying the calibration factor to numeric color values measured from the three-dimensional image itself. In addition, the system may read the unique identifier and validate the specific calibration slate used based on the unique identifier to verify that the calibration slate has not been previously used, which prevents potential cross-contamination between patients. The unique identifier is preferably in the form of a machine-readable bar code.

Once the calibration of the three-dimensional image is complete, the user will have a visual representation that accurately shows the colors of the patient wound regardless of any external factors that may affect the visual appearance of the wound, thereby giving medical professionals necessary information for accurately diagnosing and evaluating the patient. In addition, the user may manipulate the three-dimensional image to view an accurate visual representation of the contours of the wound in three dimensions. The system may also be used to measure the physical parameters, including depth, of the wound and to monitor how the wound changes over a period of time, including both the color of the wound and the depth or other parameters of the wound. Thus, the present system provides a complete and accurate visual representation of wounds or skin conditions for medical professionals and provides the ability to monitor how these characteristics change with time.

The foregoing summary has outlined some features of the system and method of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other structures for carrying out the same purpose of the system and method disclosed herein. Those skilled in the pertinent art should also realize that such equivalent designs or modifications do not depart from the scope of the system and method of the present disclosure.

DESCRIPTION OF THE DRAWINGS

These and other features, aspects, and advantages of the present disclosure will become better understood with regard to the following description, appended claims, and accompanying drawings where:

FIG. 3 shows an alternative embodiment of a calibration slate that may be utilized for calibrating three-dimensional images in accordance with the present disclosure.

FIG. 4A shows a focus chart that may be printed on a calibration slate that may be utilized for calibrating three-dimensional images in accordance with the present disclosure.

FIG. 4B shows a focus chart that may be printed on a calibration slate that may be utilized for calibrating three-dimensional images in accordance with the present disclosure.

FIG. 4C shows a focus chart that may be printed on a calibration slate that may be utilized for calibrating three-dimensional images in accordance with the present disclosure.

DETAILED DESCRIPTION

In the Summary above and in this Detailed Description, and the claims below, and in the accompanying drawings, reference is made to particular features, including method steps, of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises" and grammatical equivalents thereof are used herein to mean that other components, steps, etc. are optionally present. For example, a system "comprising" components A, B, and C can contain only components A, B, and C, or can contain not only components A, B, and C, but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Figure 1:
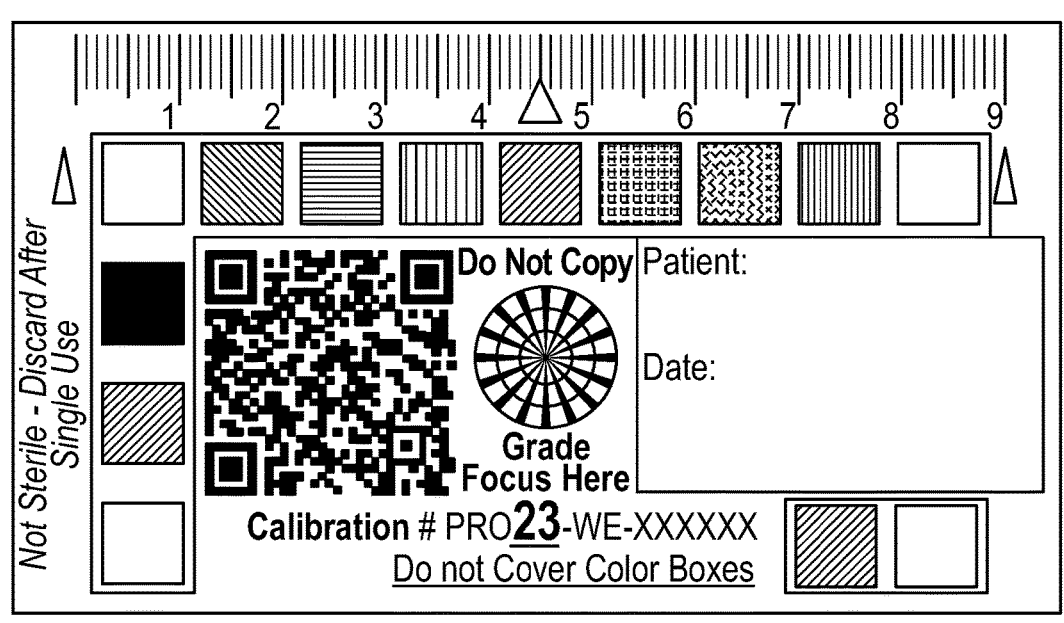
FIG. 1 shows a calibration slate that may be utilized for calibrating three-dimensional images in accordance with the present disclosure.
Figure 2:
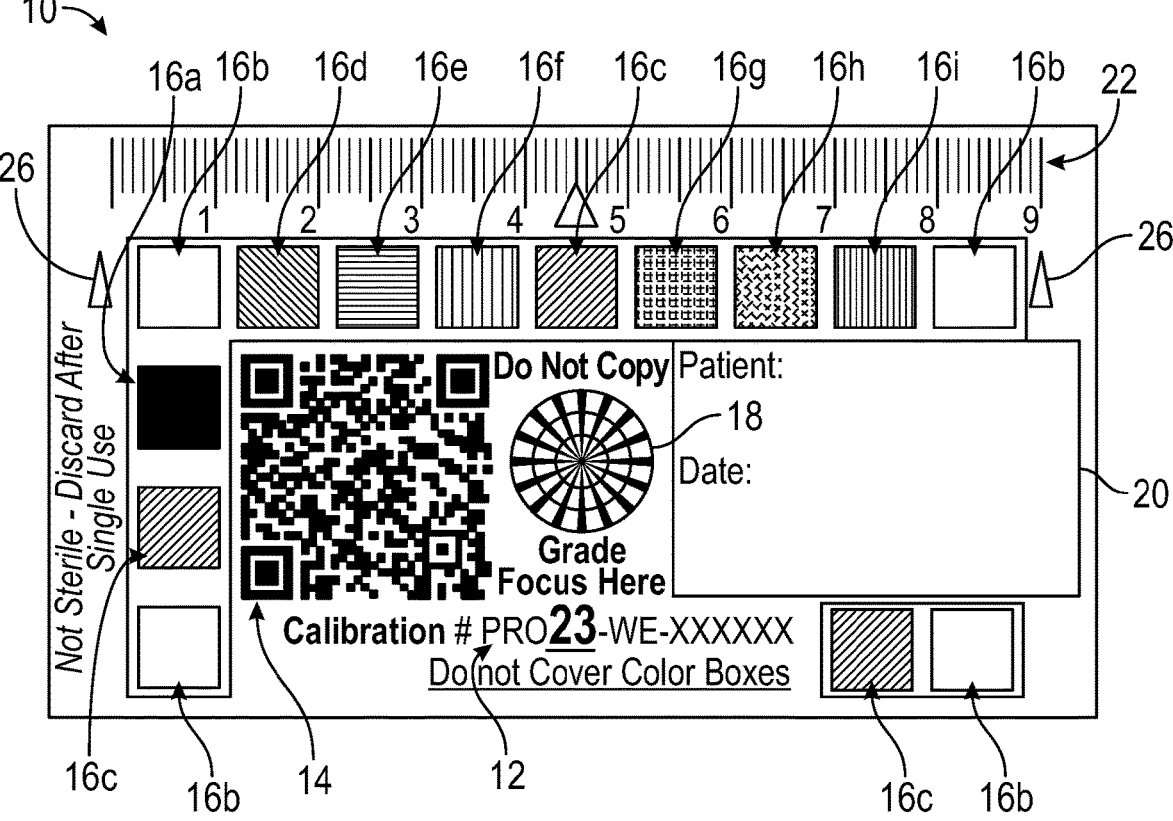
FIG. 2 shows a calibration slate that may be utilized for calibrating three-dimensional images in accordance with the present disclosure.
Figure 14:
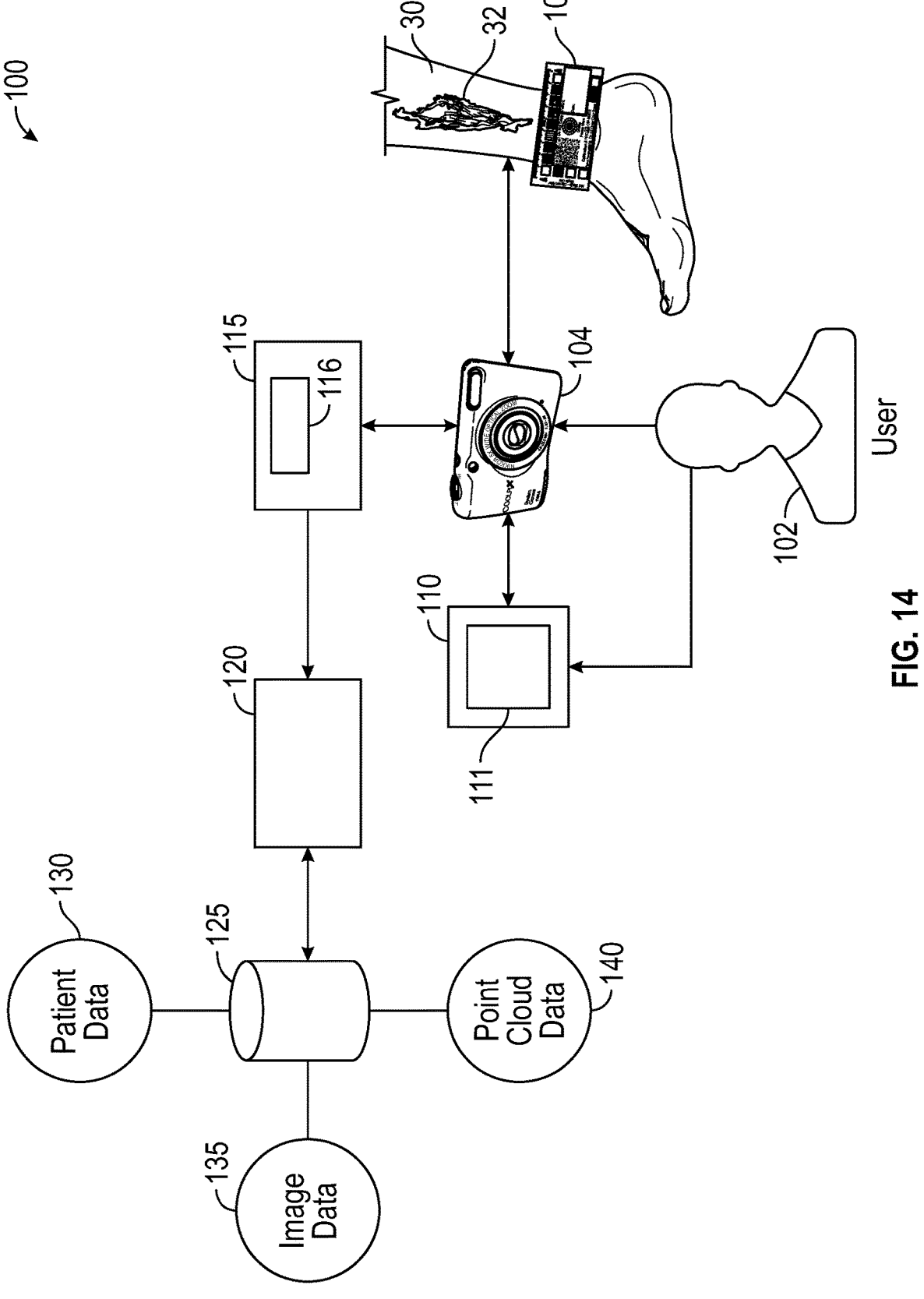
FIG. 14 shows a system for producing a three-dimensional medical image using a calibration slate in accordance with the present disclosure

A system and method of producing medical image data that provides consistently accurate visual representations of three-dimensional medical images are provided. FIG. 14 illustrates an example system 100 that may be utilized to carry out the present method of producing three-dimensional medical images using a calibration slate 10. FIG. 1 illustrates an illustrative calibration slate 10 that may be utilized in accordance with the present system 100 and method to color calibrate a three-dimensional image relating to the medical field, such as a wound or a skin condition. As used herein, the term "medical field" refers generally to any field of medicine and may include wound care, dermatology, forensic medicine, veterinary medicine, or other related medical fields, and may also include any field related treatment, evaluation, testing, or study in the medical field. FIG. 2 illustrates a calibration slate 10 with particular features of the slate identified. The calibration slate 10 includes certain features that may be utilized to calibrate an image and to validate the slate, including a print run number 12, a unique identifier 14, and a color chart 16. The color chart 16 is printed on each slate 10 and comprises at least one color and preferably a set of colors 16a-16i for color calibrating each captured image 42, which includes a calibration slate 10 appearing within the image with the color chart 16 visible in the image. The print run number 12 identifies a batch of printed calibration slates 10 comprising a plurality of separate individual slates that are all printed as part of one batch, or print run. Thus, the print run number 12 printed on a slate 10 appearing in a captured image 42 identifies a specific batch of slates that includes the calibration slate 10 appearing in each image to be calibrated. Because the slates in a batch are all printed as a group in one print run, each calibration slate 10 in the batch of printed slates is substantially similar to all slates within the batch, including the color values of all colors of the color chart 16 printed on each slate 10. Because all slates within a batch are substantially similar, associating a particular slate 10 appearing within an image 42 with a batch of slates provides a standard for comparing measured color values from the image 42 to be calibrated to the standard, which has known numeric color values, thereby facilitating accurate color calibration of the image 42 showing the calibration slate 10 in the captured image. As used herein, the term "captured image" or grammatical equivalents thereof refer to an image captured as is by an image recording device 104, such as a camera or video recorder, that has not yet been subsequently altered or manipulated by the present system 100.

In a preferred embodiment, the color chart 16 is in the form of a color matrix comprising a plurality of individual discrete boxes each printed a respective color and having a defined border and known dimensions. FIG. 1 illustrates one illustrative arrangement of the color matrix, though it should be understood that other arrangements are possible and would fall within the scope of the present disclosure. As best seen in FIG. 2, in a preferred embodiment, the color chart 16 printed on each calibration slate 10 includes respective, discrete boxes printed in the colors of black 16a, white 16b, grey 16c, green 16d, cyan 16e, magenta 16f, yellow 16g, orange 16h, and red 16i, though it should be understood that other colors may be utilized in addition to or in place of one or more of these colors and still fall within the scope of the present disclosure. One or more, and any combination of colors 16, may be utilized for color calibrating a two-dimensional or a three-dimensional image.

In a preferred embodiment, the calibration slate 10 also includes a unique identifier 14 that individually identifies the particular calibration slate 10 appearing in the image 42 to be calibrated. As shown in FIG. 2, the unique identifier is preferably in the form of a machine-readable bar code 14, which is preferably a Quick Response (QR) code. The calibration slate 10 may be validated based on the unique identifier 14, preferably by the system 100 reading the bar code 14. By validating the calibration slate 10, the system 100 verifies the source of the slate and that the specific calibration slate shown in the image to be calibrated has not been previously used for calibration, thereby preventing potential cross contamination between patients due to the calibration slate coming into physical contact with the patient when capturing the image. Each calibration slate 10 is positioned adjacent to the subject and preferably includes an adhesive strip on the back of the calibration slate for directly attaching the slate to the subject, which is the patient. The calibration slates are typically not sterilized and should thus be discarded after a single use.

In a preferred embodiment, as shown in FIG. 2, each calibration slate 10 may include a unique identifier 14 that is separate from the print run number 12. In alternative embodiments, the unique identifier 14, which is unique to each individual respective calibration slate 10, and the print run number 12, which is not unique to individual slates but is unique only to a batch comprising a plurality of individual slates all having the same print run number 12, may both be embodied within a single identifier. For instance, the bar code 14 printed on a calibration slate 10 may be unique to that individual slate, but may also include information relating to the batch of slates from which that individual slate originates. In another alternative embodiment, the print run number 12 may include a plurality of individual numeric digits, letters, or other characters, which may include the print run number identifying the batch from which that individual slate originates, as well as a series of additional characters that are unique to that individual slate 10 for the purpose of identifying only that individual slate. Thus, the print run number 12 on the calibration slate may include a series of characters that collectively provide both the print run number and the unique identifier. Although a preferred embodiment, as shown in FIG. 2, shows the print run number 12 and unique identifier 14 as separate, discrete printed elements on the calibration slate 10, it should be understood by one skilled in the art that any calibration slate having a identifying markings of any type that may be used to uniquely identify that individual slate, as well as to identify the batch of printed slates from which that individual slate originates, would be considered to include both a print run number 12 and a unique identifier 14 as these terms are used herein and would fall within the scope of the present disclosure.

FIG. 3 illustrates an alternative embodiment in which the calibration slate 10 includes only a unique bar code and a color matrix. The unique bar code identifies the individual slate and also includes information that identifies the batch of printed slates from which the slate originates. The bar code preferably has a generally rectangular shape having known dimensions (a and b) that may be used as a measurement scale when capturing an image to be calibrated. In this embodiment, the color matrix 24 comprises a minimum number of colors, which preferably include red 24a, blue 24b, and green 24c. The colors are preferably contained within boxes positioned at corners of the bar code.

In a preferred embodiment, as shown in FIG. 2, the calibration slate 10 includes a focus chart 18 comprising concentrically arranged shapes. The focus chart 18 is configured such that it can be used for grading the focus of images to be calibrated. When capturing an image, the focus chart may be utilized to aid in focusing the image to provide better images for the visual medical record. FIGS. 4A, 4B, and 4C show alternative embodiments of focus charts 18 that may be utilized on the calibration slate 10. The concentrically arranged shapes of the focus chart allow the system 100 to detect multiple levels of focus accuracy by determining how many levels inside the concentric shapes for which the system can detect fidelity and detail. Alternatively, the QR code 14 or a similar feature printed on the slate may be utilized for focusing an image. For instance, the system may read the QR code and determine whether a threshold of focus is achieved in that part of the image to be captured. This feature of the calibration slate provides focus grading that helps to determine if the focus fidelity of the image is acceptable, thereby saving time by rejecting poor, unacceptable image quality, which would result in poor or erroneous visual medical records that would not adequately serve the purpose of accurately representing the patient or subject.

In a preferred embodiment, as shown in FIG. 2, the calibration slate 10 includes a ruler 22 with measurement markers at a top end of the slate for visually measuring the dimensions of a wound 32 or other skin feature when the slate is attached to the subject 30 adjacent to the wound. The slate 10 preferably also includes arrows 26 printed on the slate and pointing upward toward the top of the slate to indicate the proper orientation of the slate when positioning the slate 10 adjacent to the subject 30 of the image. Preferably, the calibration slate 10 also includes a blank box 20 in which a medical professional may manually write notes relating to the patient who is the subject 30 of the medical image and to whom the slate 10 will be associated. This space 20 may preferably include patient identification information, such as the patient's name or other identifying information, as well as the date that the specific calibration slate 10 is used for the patient. This information may be used to associate a specific calibration slate with a particular patient. In a preferred embodiment, patient identification information may be machine-readable. Preferably, the system 100 allows a medical professional to link a calibration slate 10 to a particular patient using the bar code 14. Thus, the bar code 14 on a specific slate 10 may be scanned and linked to a particular patient including all of the patient identification information associated with the patient.

The present method generally comprises capturing one or more two-dimensional images 42 of a subject 30 on an image recording device 104 and then producing a color calibrated three-dimensional image 48 of the same subject 30 based on the one or more two-dimensional images 42. As used herein, a "three-dimensional" image refers to a three-dimensional construct, which may include three-dimensional image data, such as point cloud data, in addition to a visual skin imposed upon the three-dimensional construct to produce the image. FIG. 14 illustrates a system 100 that may be used to produce and calibrate the three-dimensional image 48. Each two-dimensional image, as well as the three-dimensional image, includes a calibration slate 10 appearing within the image. The same calibration slate 10 appears in all of the images for a single iteration of the process. Consecutive iterations of the process may be carried out at spaced time intervals, which allows both qualitative and quantitative analysis of how the wound 32 changes with time during the healing process. The process provides a complete and accurate visual representation of both the color of the wound 32 and the depth and general contours of the wound in order to allow medical professionals the ability to monitor how colors and contours of the wound change with time. Providing an accurate visual representation of both the color and contours of a wound in a three-dimensional representation gives medical professionals a complete picture of a wound as wounds generally change both in color and in depth during the healing process. Thus, accurate wound color and contour information provides medical professionals with all necessary information to provide optimal medical treatment to patients.

Figure 7:
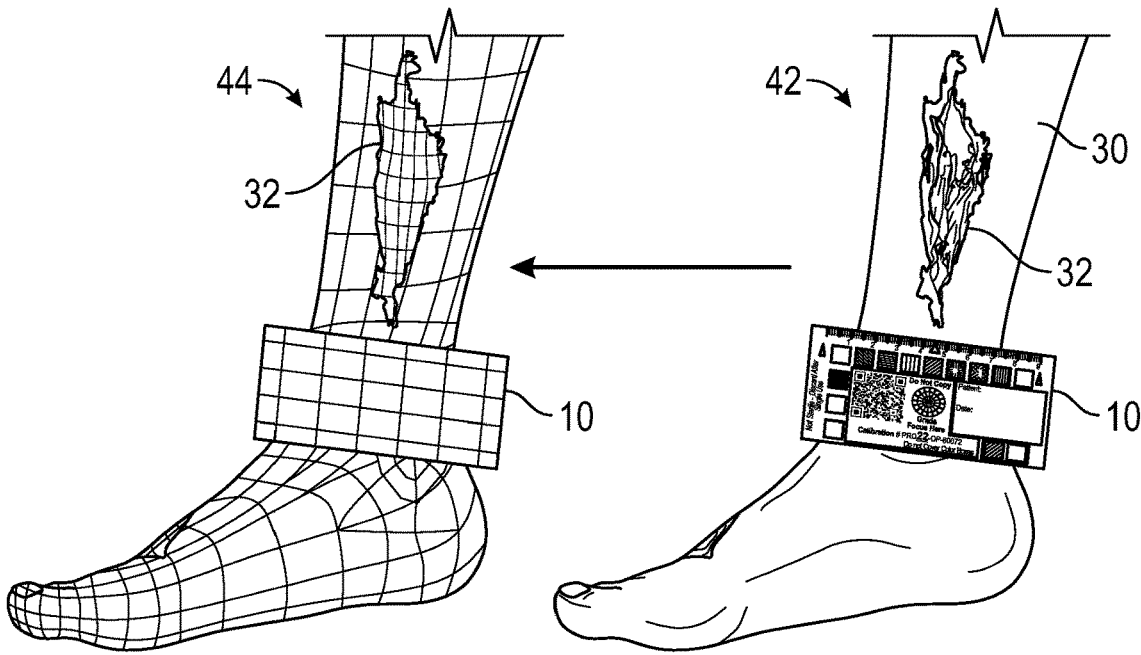
FIG. 7 shows a three-dimensional model of a subject in accordance with the present disclosure.
Figure 8:
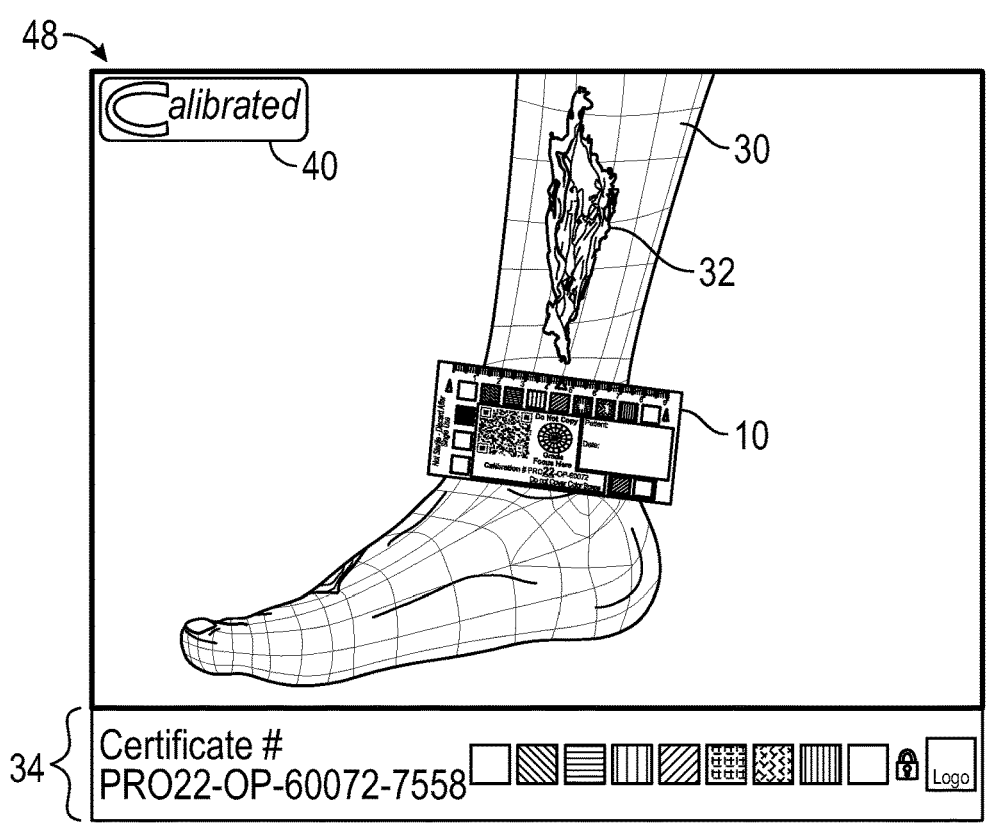
FIG. 8 shows a calibrated three-dimensional image in accordance with the present disclosure.

In a preferred embodiment, to construct a three-dimensional model 44 of the subject 30, the method includes generating point cloud data relating to the subject of each captured two-dimensional image 42, as best seen in FIG. 7. The point cloud data represent the three-dimensional shape of the subject 30, which includes the three-dimensional contours of the wound 32 of the subject. Point cloud data may be generated by capturing an image or video using a LIDAR-enhanced camera, any camera capable of capturing 3D information such as a camera sold under the trademark TrueDepth® by Apple, Inc., or any other suitable type of 3D scanner or photogrammetry software program. A three-dimensional model 44 of the subject may then be constructed utilizing the point cloud data. To construct the three-dimensional model 44, the point cloud data may be converted into a surface mesh, such as a polygon mesh, through surface reconstruction methods. Any suitable method for converting point cloud data to a three-dimensional surface mesh may be utilized, including, but not limited to, Delaunay triangulation, alpha shapes, or through a marching cubes algorithm, for instance. As best seen in FIG. 7, one or more two-dimensional images 42 may then be applied to the three-dimensional model 44 to produce the three-dimensional image 48 of the subject, as seen in FIG. 8. The three-dimensional image 48 also shows the calibration slate 10 that appears in each two-dimensional image 42 of the subject 30. As used herein, a two-dimensional image may be "applied" to a three-dimensional model by graphically laying a visual two-dimensional skin onto a surface defined by the three-dimensional model, which may include interpolation of two-dimensional image data to determine what image data may be duplicative and what data may be missing when applying a plurality of two-dimensional images to a three-dimensional model to produce a three-dimensional image of the subject, or other suitable methods of using two-dimensional images and three-dimensional models to produce three-dimensional visual representations.

Figure 5A:
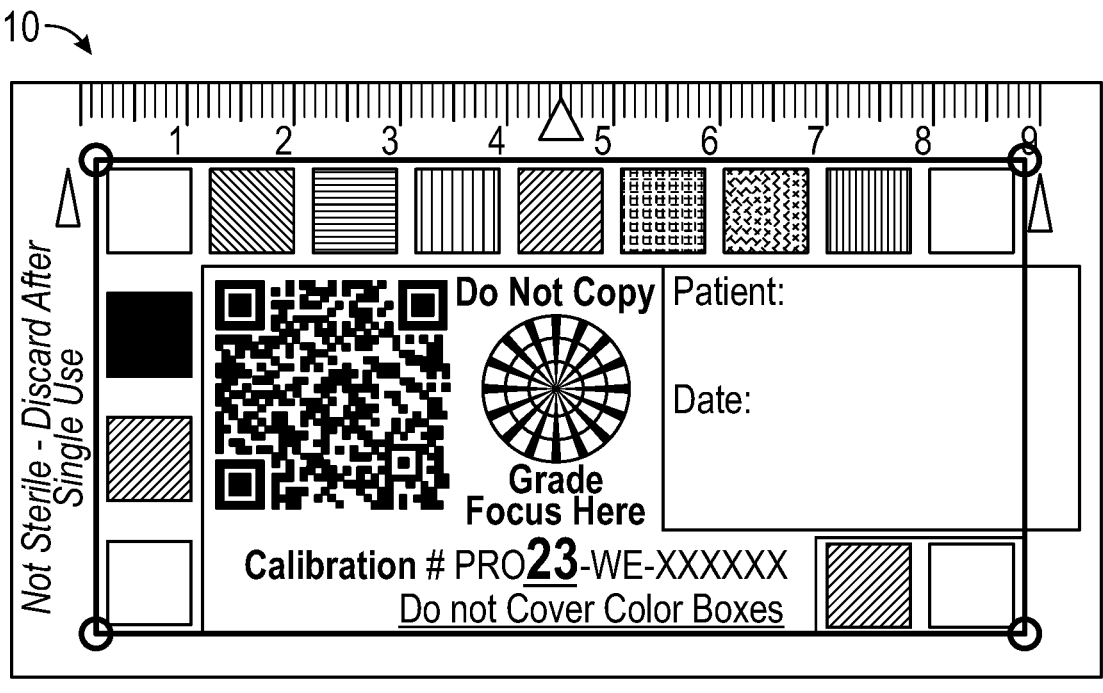
FIG. 5A shows a calibration slate that may be utilized for calibrating three-dimensional images in accordance with the present disclosure.
Figure 5B:
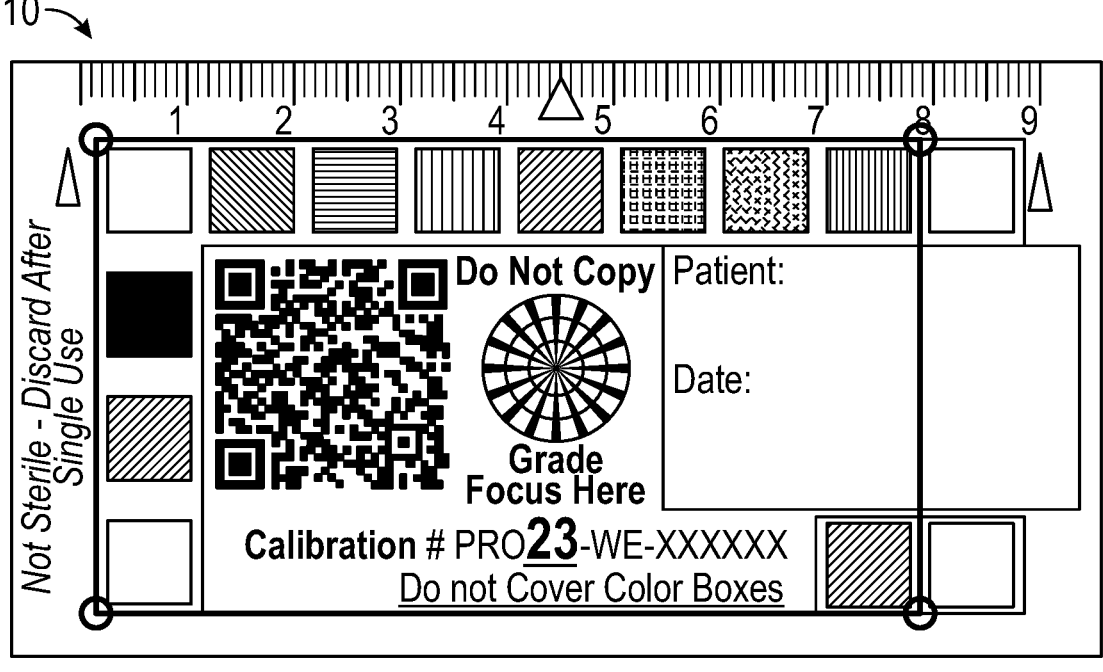
FIG. 5B shows a calibration slate that may be utilized for calibrating three-dimensional images in accordance with the present disclosure.
Figure 5C:
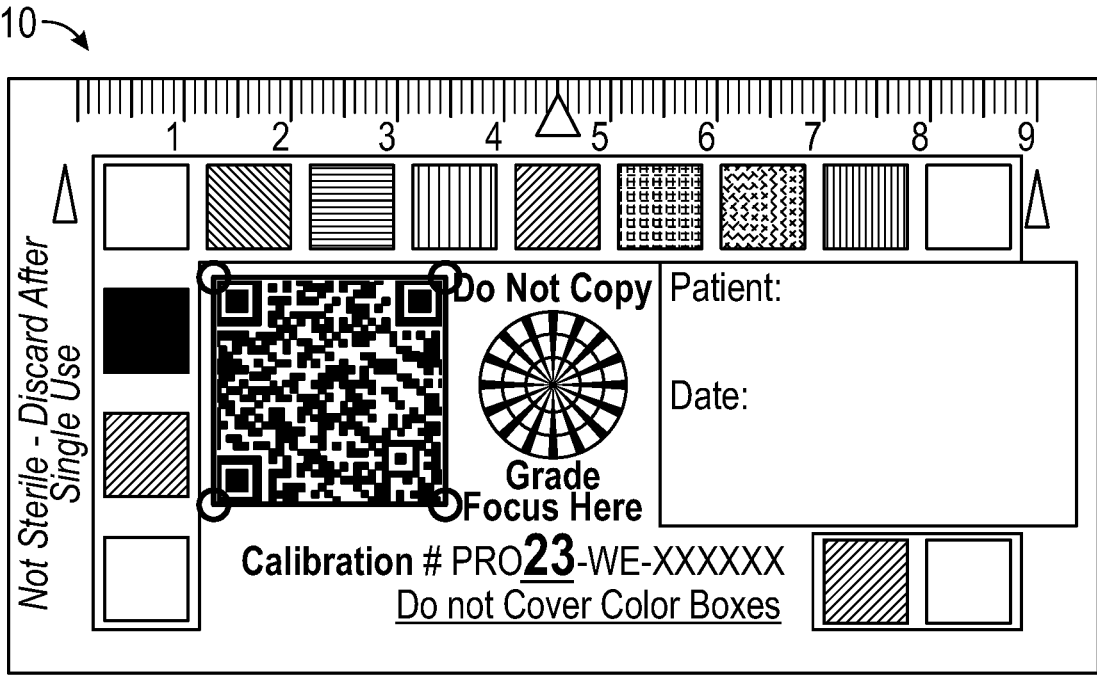
FIG. 5C shows a calibration slate that may be utilized for calibrating three-dimensional images in accordance with the present disclosure.
Figure 5D:
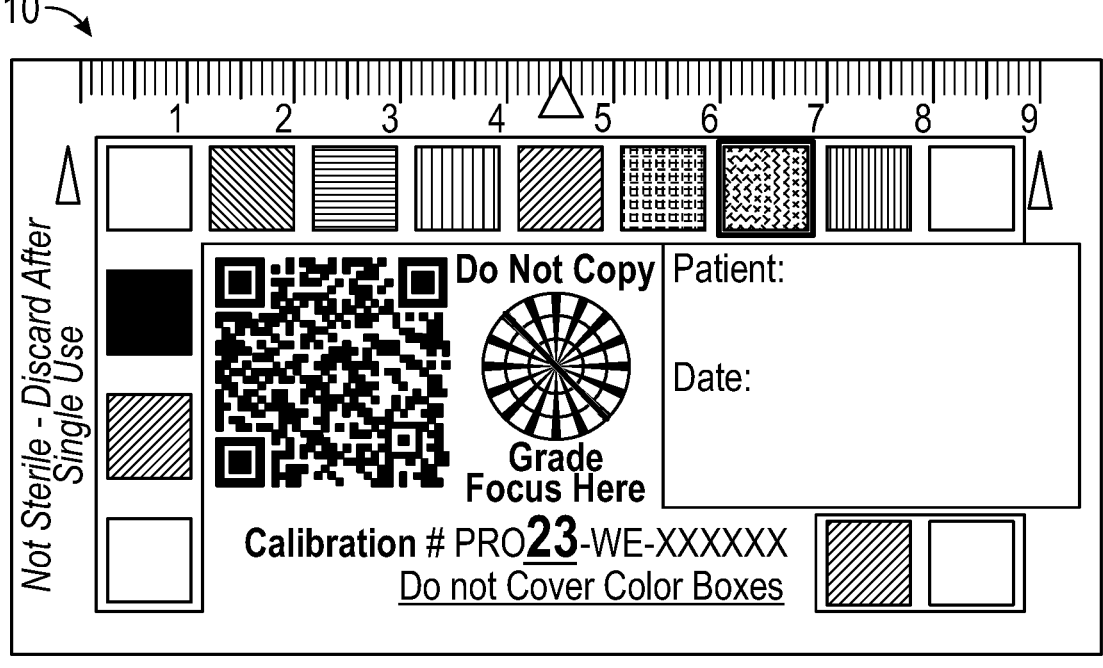
FIG. 5D shows a calibration slate that may be utilized for calibrating three-dimensional images in accordance with the present disclosure.

In some embodiments, the three-dimensional image 48 may be constructed utilizing a plurality of two-dimensional images 42 of the subject 30, which may be captured from varying angles relative to the subject, each including the same calibration slate 10 in the image, which is preferably attached to the subject. To correct skew that may occur when capturing two-dimensional images at an angle to the subject 30, the scale of objects relating to the subject and appearing in each of the two-dimensional images 42, such as the patient wound 32, may be determined based on known measurements of one or more objects printed on the calibration slate 10 that appears in each of the two-dimensional images. The calibration slate has numerous objects printed on the slate having known measurements that may be utilized to this end. FIGS. 5A-5D identify some example objects that may be utilized. For instance, FIG. 5A shows known measurements extending to the four corners of the complete color set 16, while FIG. 5B shows measurements extending to all but two of the color squares 16a-16i, or chips, on the calibration slate, with the two chips farthest to the right of the slate excluded from the measurement, which in this embodiment are both white chips 16b. In this case, these known measurements, which are truncated from the dimensions of the full color set, may be utilized if the chips farthest to the right on the slate are not adequately detected by the image recording device 104. In some cases, areas of the slate 10 having smaller known measurements may be utilized. For instance, in FIG. 5C, the dimensions of the bar code 14 are utilized. Even the dimensions of a single chip, as shown in FIG. 5D, may be utilized, which in this case is an orange chip 16h. In other cases, the known diameter of the focus chart 18 may be utilized. In a preferred embodiment, the system 100 may utilize combinations of such known measurements of objects printed on the calibration slate for skew detection and correction.

In one embodiment, the scale of objects in the image, such as the wound 32, may be determined by counting pixels or other photographic elements composing the object of known size from the calibration slate 10 shown in the image. By comparing the known measurements of the color set 16, any combination of chips within the color set, the QR code 14, the focus chart 18, or some other feature printed on the slate, or combinations thereof, to the number of pixels or other photographic elements of the object shown in the captured image 42, such as the wound 32, the system 100 may determine the scale or ratio of the known metric to the metrics of the captured image for which the scale is to be determined. Additionally, the distance measured may be a pattern or combination of objects on the calibration slate or the outer edges of the slate itself.

Figure 6:
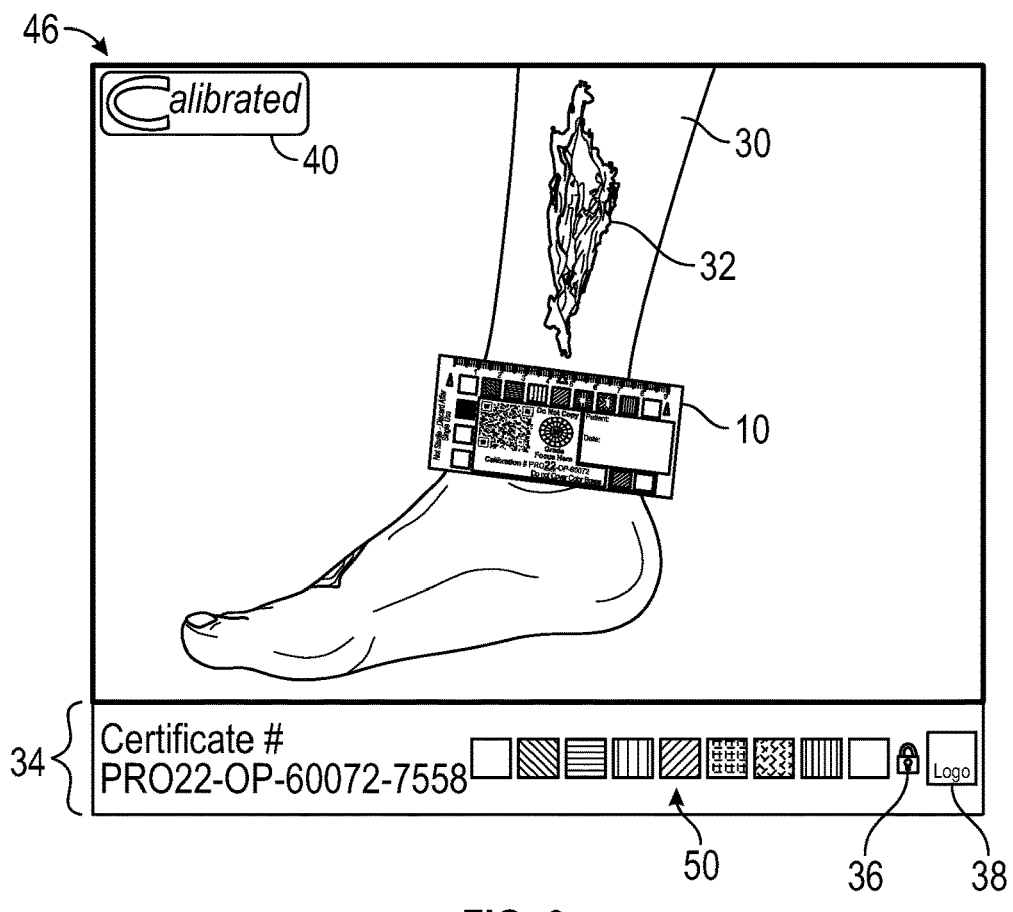
FIG. 6 shows a calibrated two-dimensional image in accordance with the present disclosure.

To color calibrate the three-dimensional image, the present method preferably begins by first using the image recording device 104 to capture one or more two-dimensional images 42 of the subject 30 with the same calibration slate 10 being shown in each image adjacent to the subject, as best shown in FIGS. 6 and 7. In a preferred embodiment, the two-dimensional images are first color calibrated before producing the three-dimensional image. Alternatively, the three-dimensional image may first be produced utilizing the one or more two-dimensional images and then calibrated. To calibrate the captured images, the system 100 may then measure numeric color values from one or more colors 16 in the color chart printed on the calibration slate 10 that appears in each captured image 42. Thus, because the calibration slate 10 appears within the image 42, as shown in the captured two-dimensional image 42 as shown in FIGS. 7 and 14 and the calibrated two-dimensional image 46 as shown in FIG. 6, color values are measured from the captured image itself 42 when measuring the color values from the calibration slate 10. The system 100 may be configured to locate and identify the calibration slate 10 within the borders of the captured image 42, which may be uploaded or transferred to the system 100 from the image recording device 104, based on identification of one or more printed elements on the slate. The system 100 may then further identify discrete colored squares 16 or other areas of the color chart on the slate 10 and further associate known color values for the slate 10 with individual respective colors 16a-16i of the color chart as shown in the captured image 42. The system 100 may then measure color values from one or more of the colors 16 of the color chart as shown in the image 42 as captured by the image recording device 104. The captured image 42 is preferably a digital photograph or other type of electronic representation, and the system 100 may identify and measure color values for each individual pixel or other similar individual picture elements of the portion of the electronic image located within the color chart 16 to measure color component intensities of individual colors, such as red, blue, and green (RBG color values), or other colors such as grey 16c, white 16b, green 16d, cyan 16e, magenta 16f, yellow 16g, orange 16h, or black 16a.

In addition, after locating and identifying the calibration slate 10 shown in the captured image 42, the system 100 may then read the print run number 12 on the calibration slate 10 and associate the print run number 12 with a batch of printed calibration slates that includes the specific calibration slate 10 appearing in the image 42. Because each calibration slate in the batch, including the slate appearing in the image 10, is substantially similar, the numeric color values measured from the color chart 16 shown in the captured image 42 have corresponding known numeric color values associated with the batch of calibration slates. The measured numeric color values from the color chart 16 shown in the image 42 may then be compared to the corresponding known numeric color values. Based on this comparison, the system 100 may calculate a variance between the numeric color values measured from the image 42 to be calibrated and the corresponding known numeric color values. The system 100 may then calculate a calibration factor based on the variance. Once a calibration factor has been determined, each image 42 may be color calibrated based on the calibration factor by adjusting the colors of the image by applying the calibration factor to numeric color values measured from the image. To this end, the system 100 may measure color values for each individual pixel or other similar individual picture elements of the entire captured image 42 to measure color component intensities throughout the image and then adjusting the color values of each pixel of the captured image 42 according to the calibration factor to calibrate the entire image. FIG. 6 shows a color calibrated and certified two-dimensional image 46 of a subject 30 with wound 32 on the leg of a patient.

Because the calibration slate 10 with colors 16 is placed within the same area of the captured image, the colors on the slate are subject to the same unknown conditions of the environment (including lighting, camera settings, and camera software manipulation). Thus, the system 100 can compare measured color values from the image (from the calibration slate portion of the image) with known standards from the printed calibration slates to determine the calibration factor that can be applied to the entire image including both the subject 30 and the slate 10. Any single color from the color chart printed on the slate may be used to calibrate the entire image, or more than one color may be used. In one embodiment, a medium grey and/or a white may be utilized. Both white and grey are a blend or mix of all colors and are more noticeable to the eye when changed as compared to black because of its density of color. For instance, if a grey was known to have a same value of 125 in red, green, and blue (RGB), then it would be neutral grey that is evenly mixed of all three. Likewise, if the grey color was in the middle of the gray scale, then it would contain a rich amount of data in the middle of both the visible RGB scale and the grey scales, thus making it a good candidate for calibration of the image.

Although any single known color may be used for calibration, in some embodiments, certain colors may be selected as having particular relevance to the subject, such as red for medical subjects with blood vessels present, which may make certain colors better candidates for medical-related image calibration. For instance, certain colors may be selected for particular relevance to the subject and the process to maximize the data, outcome, and ability for the user to identify items of value in the medical field. For example, yellow, magenta, orange, and red are all common in many medical subjects and often correlate to diagnostic characteristics such as red indicating edema, infection, or granulated tissue with good blood flow. Yellow is often the color of slough or puss. Therefore, these colors are likely relevant to a medical subject. If these colors are calibrated and appear to match their corresponding known colors once the image is calibrated, than this would indicate that those colors in the subject image are likewise presented accurately. Alternatively, if the colors of the captured image are calibrated to within a predetermined tolerance or margin of error from the known color values, then the image may be determined to color calibrated.

Figure 9:
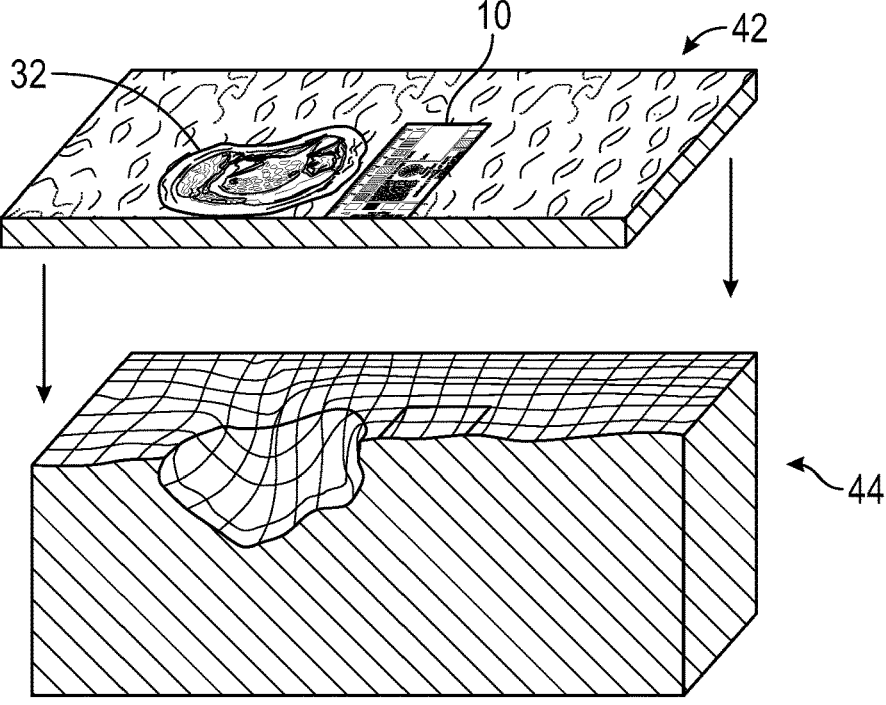
FIG. 9 shows a three-dimensional model of a subject in accordance with the present disclosure.

Next, a three-dimensional image may be produced utilizing the one or more two-dimensional images 42, preferably also utilizing point cloud data. As best seen in FIGS. 7 and 9, one or more two-dimensional images 42, which have preferably first been color calibrated in accordance with the present method to produce a color calibrated two-dimensional image 46, may be applied to a three-dimensional model 44 constructed utilizing the point cloud data relating to the subject 30 to produce a color calibrated three-dimensional image 48. FIG. 8 illustrates the three-dimensional image 48 within a graphical display after the image has been color calibrated and certified, as indicated by the lower certification display 34. Once the calibration of the three-dimensional image 48 is complete, the user will have a three-dimensional visual representation that accurately shows the colors of the patient wound 32 regardless of any external factors that may affect the visual appearance of the wound, thereby giving medical professionals necessary information for accurately diagnosing and evaluating the patient. In addition, the user may manipulate the three-dimensional image 48 to view an accurate visual representation of the contours of the wound 32 in three dimensions.

Figure 10:
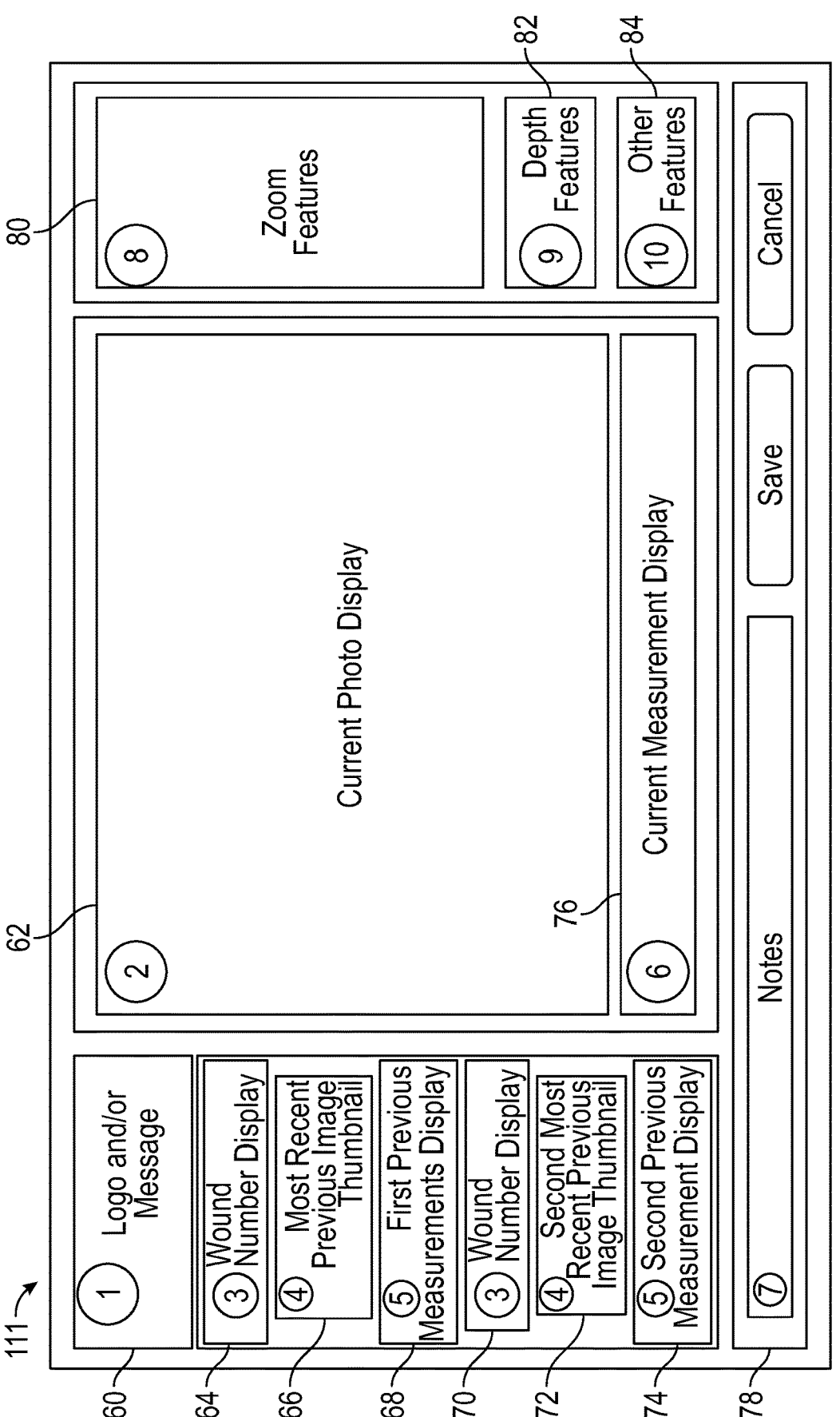
FIG. 10 shows a graphical user interface that may be used with a system for calibrating three-dimensional images in accordance with the present disclosure.
Figure 11:
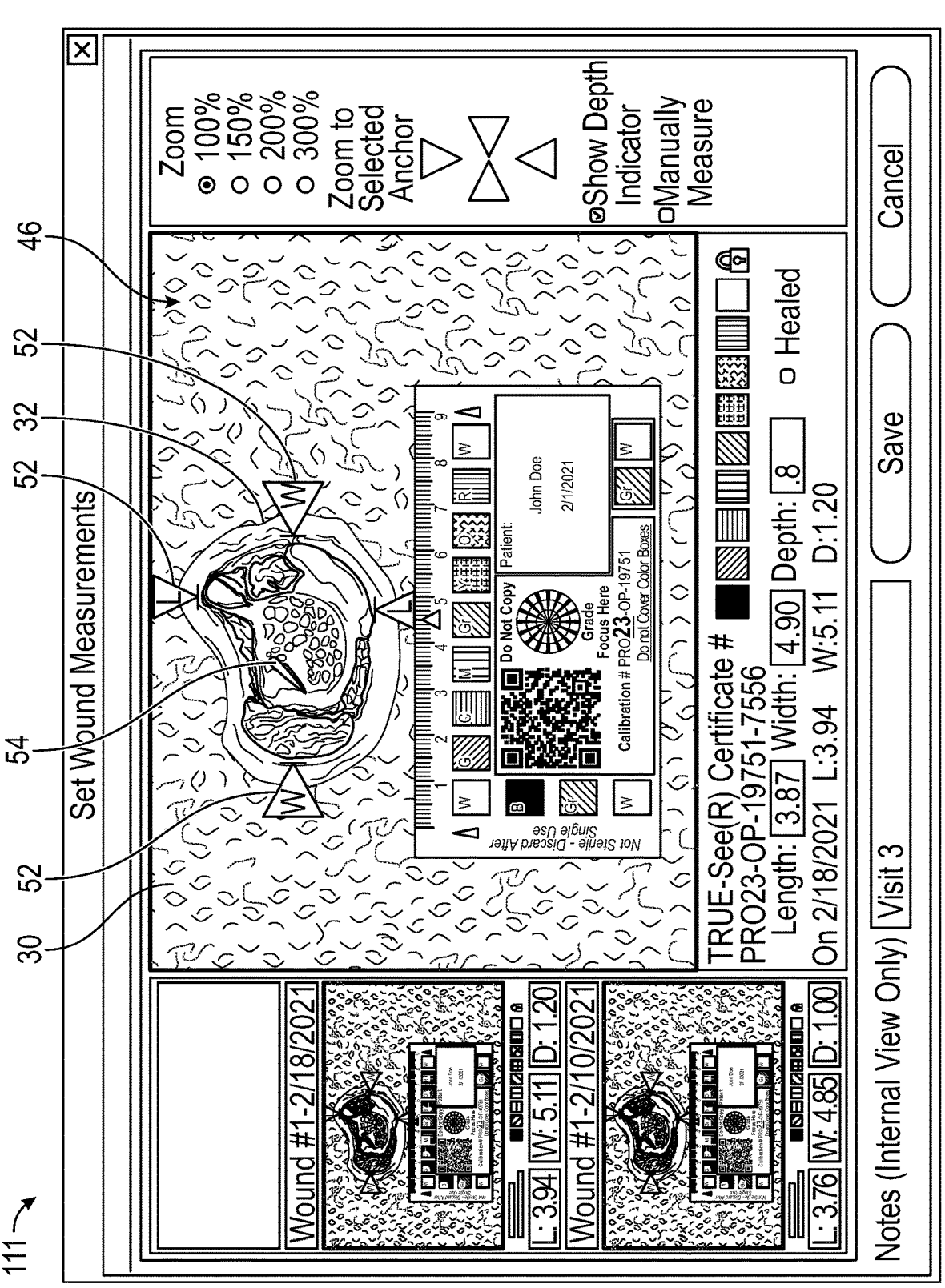
FIG. 11 shows a graphical user interface showing a calibrated two-dimensional image in accordance with the present disclosure.
Figure 12:
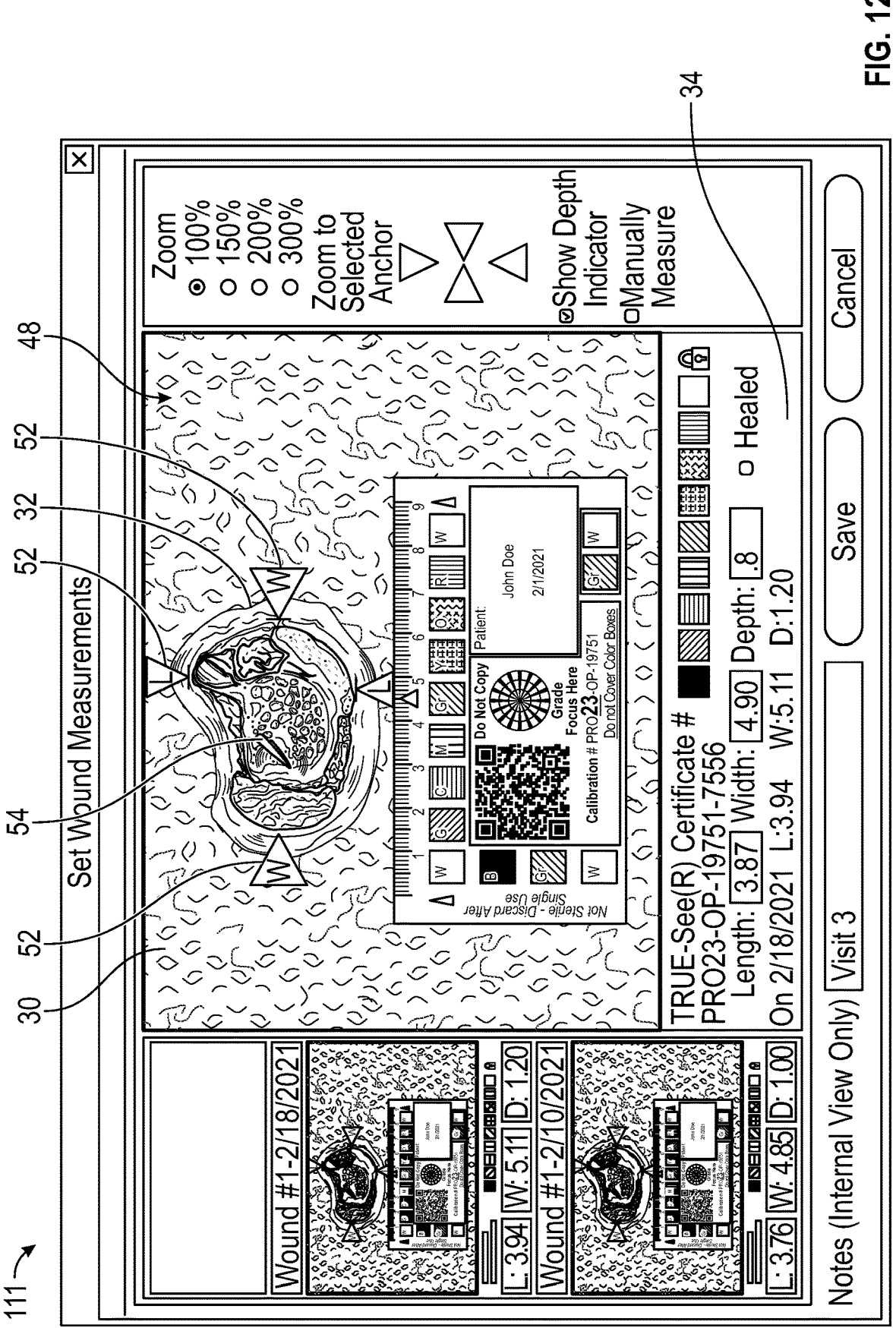
FIG. 12 shows a graphical user interface showing a calibrated three-dimensional image in accordance with the present disclosure.

FIG. 9 illustrates another example of applying a two-dimensional image 42 of a wound 32 to a three-dimensional model 44 to produce a three-dimensional image 48. As shown in FIG. 9, the wound 32 has a depth that is represented by the three-dimensional model 44. This wound depth will change with time as the healing process occurs. FIG. 10 illustrates an example graphical user interface 111 that may be utilized for a user 102 to interact with the system 100. FIG. 11 illustrates the two-dimensional image shown in FIG. 9 within the graphical user interface 111 after the image 46 has been color calibrated. FIG. 12 illustrates a color calibrated three-dimensional image 48 produced by applying the two-dimensional image 42 to the three-dimensional model 44 as shown in FIG. 9. The color calibrated three-dimensional image 48 is shown within the same graphical user interface 111 after the image has been color calibrated. FIG. 12 illustrates the three-dimensional image 48 from one specific angle, though the three-dimensional image 48 may be rotated, tilted, or otherwise manipulated within the graphical user interface 111 to allow the user 102 the ability to view the contours of the wound in three dimensions and to see the wound 32 with calibrated colors.

Figure 13:
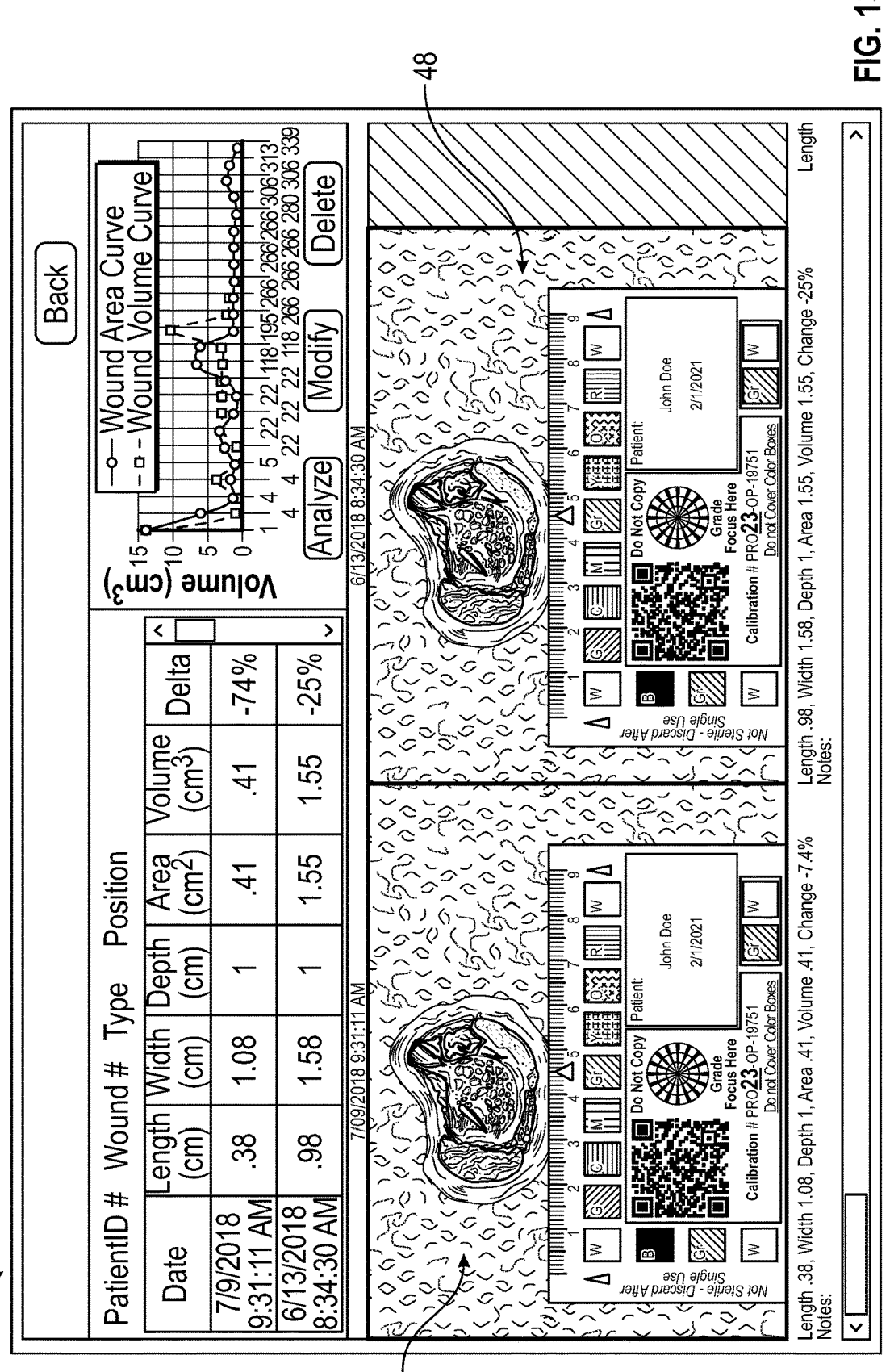
FIG. 13 shows a graphical user interface showing multiple calibrated three-dimensional images illustrating changes in a patient wound over a period of time in accordance with the present disclosure.

FIG. 10 illustrates an example graphical user interface 111 having multiple internal windows before being populated with images and other information relating to the subject 30. Window 60 provides a space for a business logo and/or a message to a user 102 relating to the system 100. Window 62 is the primary window in which images may be displayed, including color calibrated two-dimensional 46 and three-dimensional images 48, as well as captured images 42. Three-dimensional images 48 may be manipulated by the user 102 within this window 62. Windows 66 and 72 may display thumbnail views of previously calibrated images of the subject 30 at different time intervals, as indicated by the date shown in windows 64 and 70, which also display a wound number associated with the wound 32. Additional iterations of the present method may be performed at various time intervals to consecutively produce additional calibrated three-dimensional images 48 of the same subject 30 to observe changes in the subject in three dimensions over a period of time. Each additional calibrated three-dimensional image 48 includes a unique calibration slate 10 used for each iteration of the method. Thus, the additional images are each independently color calibrated using a different slate 10 each time. Each of the calibrated three-dimensional images 48 of the subject 30 may then be compared to a preceding calibrated image 48 to qualitatively determine how the subject 30 has changed over time. The system 100 may allow the user to view multiple three-dimensional images 48 of the same subject 30 sorted by date within the graphical user interface 111, as shown in FIG. 12. The system 100 preferably includes an additional interface 111 specifically for viewing all iterations of the calibrated images 48, as shown in FIG. 13, which illustrates two calibrated three-dimensional images 48 of a subject 30 that were produced on different dates, which are labeled above each three-dimensional image so that a medical professional may view changes in the wound side-by-side and scroll though all iterations to evaluate progress in healing. As shown in FIG. 13, this interface 111 may show additional information relating to the wound, such as information relating to the dimensions of the wound.

The graphical user interface 111 shown in FIG. 10 may also have a window 80 having zoom view features for enabling a user 102 to manipulate the image shown in the primary window 62. The interface 111 may also include windows 82, 84 relating to depth features and other various features of the calibrated image. The interface 111 may also have a window 78 for adding general notes relating to the patient and/or images.

The system 100 may also be used to measure the physical parameters, including depth, of the wound 32, which allows the user 102 to monitor how the wound changes with time, including both the color of the wound and the depth or other parameters of the wound. Thus, the present system 100 provides a complete and accurate visual representation of wounds 32 or skin conditions for medical professionals and provides the ability to monitor how these characteristics change with time. As shown in FIGS. 11 and 12, the interface 111 may include movable anchor points 52 that may be used to measure certain dimensions of the wound, such as length and width. The measurements of wound parameters may be calculated according to determinations of the scale of objects in the image, such as the wound, based on known measurements of objects printed on the calibration slate 10 such as the ruler 22 or bar code 14. When moving the anchor points 52 to the appropriate positions, the system 100 may automatically display measurements in windows 68, 74, and 76, which display different iterations of the calibrated images. Measurement information may also be automatically displayed in the interface 111 shown in FIG. 13, which may include graphical representations showing how an area and a volume of the wound change with time to graphically assess wound progress. Wound volume may be based on the depth of the wound, which may be calculated based on three-dimensional model 44 data. As shown in FIGS. 11 and 12, the interface 111 may also include a movable depth indicator 54, which the user 102 may position at a location on the image of the wound to indicate the wound depth at that location. The depth indicator 54 may also be used to mark locations for other purposes, such as the location of a particular procedure performed on the patient. These locations may be saved for later viewing. The depth indicator 54 may also be used to indicate any three-dimensional point on the three-dimensional image 48. The visibility of a depth indicator 54 may be turned on or off by the user.

Before using a calibration slate 10 to calibrate an image, the system 100 may also be used to read the unique identifier 14, which is preferably a machine-readable bar code, and validate the specific calibration slate 10 used based on the unique identifier 14 to verify that the calibration slate 10 has not been previously used prior to capturing two-dimensional images 42 of the subject 30, which prevents potential cross-contamination between patients. The bar code 14 on each unique slate 10 links to information related to each slate, and the system 100 may be configured to determine whether a specific slate has been used in a calibrated image and alert a user if the slate has been previously used so that each individual slate is used only once. Validating the calibration slate 10 may also indicate that the slate 10 is an original slate from a known source. Validating the calibration slate 10 may also indicate that the slate 10 is not being used in a restricted manner, which may be indicated by validating who is using the slate, where the slate is being used, and when the slate is being used.

After calibrating an image 48, the system 100 may also be used to certify that the image has been processed and properly calibrated. In a preferred embodiment, as best seen in FIGS. 6 and 8, the system 100 may graphically attach a certification bar 34, which may provide certain information relating to the image, to the calibrated image 46, 48 including the calibration slate 10. The certification bar 34 preferably includes a second color chart 50, wherein the second color chart 50 comprises a set of colors having known numeric color values. Each color in the set of colors is substantially similar to a respective corresponding color associated with the batch of calibration slates from which the slate 10 in the image originates. Because the second color chart 50 is not part of the original image, attaching this second color chart allows a user 102 to make a qualitative visual comparison of the colors on the second color chart 50 to the colors on the slate 10 in the image to qualitatively assess the quality of the color calibrated image instantaneously. In addition, as shown in FIGS. 6 and 8, after calibrating the image the system 100 may add a unique certificate number to the attached certification panel 34 that provides a confirmable indication that the image is certified as being processed and calibrated by the system 100. The certificate number is preferably machine-readable and the image may be automatically certified by reading the unique certificate number. The system 100 may also add a hash code to each certified image to provide an indication that the image has not been altered or tampered with in any way. The hash code may be visually indicated by an element in the certification bar 34 such as a lock icon 36 indicating that the image may not be altered. Alternatively, other suitable security features that prohibit and/or detect alterations to the certified image may be utilized to prevent unauthorized alterations to the image. The certification bar 34 attached to the certified image preferably also includes a logo box 38, which may be used to add a logo of a client utilizing the system 100 to visually indicate a client's identity to a system administrator. The certification bar 34 may be toggled on and off by the user.

In a preferred embodiment, as shown in FIGS. 6 and 8, the system 100 may additionally add a watermark 40, which is preferably shown in an upper or lower corner of a calibrated image. The watermark 40 may indicate "calibrated" for a calibrated image, as shown in FIGS. 6 and 8. In other cases, the watermark 40 could indicate that an image is not calibrated, or it could indicate any improper use of the system 100, such as the use of an invalid calibration slate 10 or if a user has an invalid license. The watermark 40 may be added automatically by the system 100 based on the status of the image shown in the interface 111. As used herein, a "watermark" may refer to any visible security feature embedded in the image.

Before using any calibrations slates 10 from a batch of printed slates, the system 100 may verify that all slates within the batch are substantially similar to ensure that the print run of slates produced slates with colors having consistent color values. Corresponding numeric color values may be measured directly from a plurality of respective slates within the batch. A variance may then be calculated between the numeric color values measured from each of the slates. The plurality of slates within the batch would be verified to be substantially similar if the variance is within an acceptable range, which would indicate that each individual slate 10 of the batch is suitable for use in calibrating the color of an image.

FIG. 14 illustrates a system 100 that may be used to carry out the present method of producing color calibrated three-dimensional medical images. As illustrated in FIG. 14, the system 100 generally comprises a camera 104, a calibration slate 10, a processor 115 operably connected to the camera 104, a power supply, and a non-transitory computer-readable medium 116 coupled to the processor 115 and having instructions stored thereon, which, when executed, perform method steps of the present method. The system 100 may also comprise a computing device 110, wherein said computing device may comprise a user interface 111 that may allow a user 102 to view data of the system 100 and/or cause the system 100 to perform an action via commands input by said user 102. In another embodiment, the system 100 may comprise a database 125 operably connected to the processor 115, which may be used to store patient data 130, image data 135, and three-dimensional point cloud data 140 therein. Alternatively, the patient data 130, image data 135, and point cloud data 140 may be stored on the non-transitory computer-readable medium 116. In yet another preferred embodiment, a server 120 may be operably connected to the database 125 and processor 115, facilitating the transfer of information between the processor 115 and database 125. Although represented as a single server 120 and database 125 in FIG. 14, it is understood that multiple servers and databases may be used without departing from the inventive subject matter herein.

As used herein, a database 125 refers to a set of related data and the way it is organized. Access to this data is usually provided by a database management system (DBMS) consisting of an integrated set of computer software that allows users to interact with one or more databases and provides access to all of the data contained in the database. The DBMS provides various functions that allow entry, storage and retrieval of large quantities of information and provides ways to manage how that information is organized. Because of the close relationship between the database 125 and the DBMS, as used herein, the term database refers to both a database and DBMS. The database may be operably connected to the processor via wired or wireless connection. The database may be a relational database such that the patient data 130, image data 135, and three-dimensional point cloud data 140 may be stored, at least in part, in one or more tables. Alternatively, the database 125 may be an object database such that patient data 130, image data 135, and three-dimensional point cloud data 140 may be stored, at least in part, as objects. In some instances, the database 125 may comprise a relational and/or object database and a server dedicated solely to managing the patient data 130, image data 135, and three-dimensional point cloud data 140 in the manners disclosed herein.

As depicted in FIG. 14, one embodiment of the system 100 may comprise a server 120. Although shown as a single server in FIG. 14, a server may, in some implementations, be implemented as multiple devices interlinked together via a network, wherein the devices connected to the network may be distributed over a large geographic area and performing different functions or similar functions. For instance, two or more servers may be implemented to work as a single server performing the same tasks. Alternatively, one server may perform the functions of multiple servers. For instance, a single server may perform the tasks of a web server and an indexing server.

Additionally, it is understood that multiple servers may be used to operably connect the processor 115 to the database 125 and/or other content repositories. The processor 115 may be operably connected to the server 120 via wired or wireless connection. Types of servers that may be used by the system include, but are not limited to, search servers, document indexing servers, and web servers, or any combination thereof.

Search servers may include one or more computing entities designed to implement a search engine, such as a documents/records search engine, general webpage search engine, etc. Search servers may, for example, include one or more web servers designed to receive search queries and/or inputs from users, search one or more databases in response to the search queries and/or inputs, and provide documents or information, relevant to the search queries and/or inputs, to users. In some implementations, search servers may include a web search server that may provide webpages to users, wherein a provided webpage may include a reference to a web server at which the desired information and/or links are located. The references to the web server at which the desired information is located may be included in a frame and/or text box, or as a link to the desired information/document. Document indexing servers may include one or more devices designed to index documents available through networks. Document indexing servers may access other servers, such as web servers that host content, to index the content. In some implementations, document indexing servers may index documents/records stored by other servers connected to the network. Document indexing servers may, for example, store and index content, information, and documents relating to user accounts and user-generated content. Web servers may include servers that provide webpages to clients. For instance, the webpages may be HTML-based webpages. A web server may host one or more websites. As used herein, a website may refer to a collection of related webpages. Frequently, a website may be associated with a single domain name, although some websites may potentially encompass more than one domain name. The concepts described herein may be applied on a per-website basis. Alternatively, in some implementations, the concepts described herein may be applied on a per-webpage basis.

The processor 115 may comprise any type of conventional processor or microprocessor that interprets and executes computer readable instructions. The processor 115 is configured to perform the operations disclosed herein based on instructions stored within the system 100. The processor 115 may process instructions for execution within the computing entity 110, including instructions stored in memory or on a storage device, to display graphical information for a graphical user interface (GUI) 111 on an external peripheral device, such as a display. The processor 115 may provide for coordination of the other components of a computing entity 110, such as control of user interfaces 111, applications run by a computing entity, and wireless communication by a communication interface of the computing entity. The processor 115 may be any processor or microprocessor suitable for executing instructions. In some embodiments, the processor 115 may have a memory device therein or coupled thereto suitable for storing the data, content, or other information or material disclosed herein. In some instances, the processor 115 may be a component of a larger computing device. A computing device 110 that may house the processor therein may include, but are not limited to, laptops, desktops, workstations, personal digital assistants, servers, mainframes, cellular telephones, tablet computers, smart televisions, streaming devices, or any other similar device. Accordingly, the inventive subject matter disclosed herein, in full or in part, may be implemented or utilized in devices 110 including, but are not limited to, laptops, desktops, workstations, personal digital assistants, servers, mainframes, cellular telephones, tablet computers, smart televisions, streaming devices, or any other similar device.

As mentioned previously, the processor 115 is configured to perform the operations disclosed herein based on instructions stored within the system 100. In an embodiment, the programming instructions responsible for the operations carried out by the processor are stored on a non-transitory computer-readable medium ("CRM") 116, which may be coupled to the server 115, as illustrated in FIG. 14. Alternatively, the programming instructions may be stored or included within the processor 115. Examples of non-transitory computer-readable mediums 116 include, but are not limited to, magnetic media such as hard disks, floppy disks, and magnetic tape; optical media such as CD ROM discs and DVDs; magneto-optical media such as optical discs; and hardware devices that are specifically configured to store and perform programming instructions, such as read-only memory (ROM), random access memory (RAM), flash memory, and the like. In some embodiments, the programming instructions may be stored as modules within the non-transitory computer-readable medium 116.

As mentioned previously, one embodiment of the system 100 may further comprise a computing device 110 operably connected to the processor 115. A computing device 110 may be implemented in a number of different forms, including, but not limited to, servers, multipurpose computers, mobile computers, etc. For instance, a computing device 110 may be implemented in a multipurpose computer that acts as a personal computer for a user 102, such as a laptop computer. For instance, components from a computing device 110 may be combined in a way such that a mobile computing device is created, such as mobile phone. Additionally, a computing device may be made up of a single computer or multiple computers working together over a network. For instance, a computing device may be implemented as a single server or as a group of servers working together over and Local Area Network (LAN), such as a rack server system. Computing devices may communicate via a wired or wireless connection. For instance, wireless communication may occur using a Bluetooth, Wi-Fi, or other such wireless communication device.

In an embodiment, the system may further comprise a user interface 111. The user interface 111 may be defined as a space where interactions between a user 102 and the system 100 may take place. In a preferred embodiment, the interactions may take place in a way such that a user may control the operations of the system 100, and more specifically, allow a user 102 to capture images of a subject 30, upload and view images of the subject 30, and generate, view, and manipulate three-dimensional images of the subject 30, which may include a patient wound 32 or other skin condition of the patient. A user 102 may input instructions to control operations of the system 100 manually using an input device. For instance, a user 102 may choose to alter or manipulate images presented via displays of the system 100 by using an input device of the system, including, but not limited to, a keyboard, mouse, or touchscreen. A user interface 111 may include, but is not limited to, operating systems, command line user interfaces, conversational interfaces, web-based user interfaces, zooming user interfaces, touch screens, task-based user interfaces, touch user interfaces, text-based user interfaces, intelligent user interfaces, and graphical user interfaces, or any combination thereof. The system 100 may present data of the user interface 111 to the user 102 via a display operably connected to the processor 115.

Information presented via a display may be referred to as a soft copy of the information because the information exists electronically and is presented for a temporary period of time. Information stored on the non-transitory computer-readable medium 116 may be referred to as the hard copy of the information. For instance, a display may present a soft copy of a visual representation of display data via a liquid crystal display (LCD), wherein the hard copy of the visual representation of display data may be stored on a local hard drive. For instance, a display may present a soft copy of user data, wherein the hard copy of the user data is stored within a database. Displays may include, but are not limited to, cathode ray tube monitors, LCD monitors, light emitting diode (LED) monitors, gas plasma monitors, screen readers, speech synthesizers, haptic suits, speakers, and scent generating devices, or any combination thereof, but is not limited to these devices.

It is understood that versions of the present disclosure may come in different forms and embodiments. Additionally, it is understood that one of skill in the art would appreciate these various forms and embodiments as falling within the scope of the invention as disclosed herein.

What is claimed is:

1. A method of calibrating an image related to the medical field, said method comprising the steps of:

capturing an image on an image recording device, wherein the captured image includes a calibration slate appearing in the captured image, wherein the calibration slate has a print run number that identifies a batch of printed calibration slates which includes the calibration slate appearing in the captured image, a unique identifier that individually identifies the calibration slate appearing in the captured image, and a color chart comprising at least one color;

reading the unique identifier and validating the calibration slate based on the unique identifier;

measuring a numeric color value from the at least one color in the color chart of the calibration slate appearing in the captured image;

reading the print run number;

associating the print run number with the batch of printed calibration slates which includes the calibration slate appearing in the image, wherein each calibration slate in the batch is substantially similar, wherein the measured numeric color value has a corresponding known numeric color value associated with the batch of calibration slates;

comparing the measured numeric color value to the corresponding known numeric color value;

calculating a variance between the measured numeric color value and the corresponding known numeric color value;

calculating a calibration factor based on the variance between the measured numeric color value and the corresponding known numeric color value; and color calibrating the captured image by adjusting the colors of the captured image to produce a calibrated image, wherein the colors of the captured image are adjusted by applying the calibration factor to numeric color values measured from the captured image; and embedding in the calibrated image: the measured numeric color value, the corresponding known numeric color value, the variance, the calibration factor, an adjusted numeric color value of one or more of the colors adjusted in the color calibrating step, or any combination thereof.

2. The method of claim 1, wherein the unique identifier is machine-readable.

3. The method of claim 1, wherein the step of validating the calibration slate comprises verifying if the calibration slate was previously used for calibrating an image.

4. The method of claim 1, further comprising the step of determining the scale of objects relating to a subject and appearing in the captured image based on known measurements of one or more objects printed on the calibration slate appearing in the captured image.

5. The method of claim 1, further comprising the steps of:

consecutively capturing one or more additional images of a subject, wherein the subject is the same subject in each of the one or more additional captured images, wherein each of the one or more additional captured images includes a calibration slate appearing in each of the one or more additional captured images, respectively, independently color calibrating each of the one or more additional captured images to produce one or more additional calibrated images, and comparing each of the one or more additional calibrated images to the preceding calibrated image to determine how the subject has changed over time.

6. The method of claim 1, further comprising the steps of: measuring a plurality of corresponding numeric color values directly from a plurality of respective calibration slates within the batch of printed calibration slates, and calculating the variance between the plurality of numeric color values measured from the plurality of respective calibration slates to verify that all slates within the batch are substantially similar.

7. The method of claim 1, further comprising the step of graphically attaching a second color chart to the captured image including the calibration slate, wherein the second color chart comprises a set of colors having known numeric color values, wherein each color in the set of colors on the second color chart is substantially similar to a respective corresponding color associated with the batch of calibration slates.

8. The method of claim 1, further comprising the step of attaching the calibration slate to a subject using an adhesive attached to the calibration slate before capturing the image that includes the calibration slate.

9. The method of claim 1, further comprising the step of associating the calibration slate appearing in the captured image with a patient based on patient identification information included on the calibration slate.

10. The method of claim 9, wherein the patient identification information is machine-readable, wherein the method further comprises the step of reading the patient identification information.

11. The method of claim 1, wherein the calibration slate appearing in the captured image further includes a focus chart comprising concentrically arranged shapes, wherein the focus chart is configured such that it can be used for grading the focus of the captured image, wherein the method further comprises the step of focusing the captured image using the focus chart before capturing the image.

12. The method of claim 1, further comprising the step of embedding a visible or invisible security mark in the calibrated image, wherein the security mark is configured to indicate whether the calibrated image has been altered.

13. The method of claim 1, further comprising the steps of: embedding a visible or invisible machine-readable unique number in the calibrated image that indicates that the calibrated image is certified, and certifying the calibrated image by reading the unique number.

14. The method of claim 1, further comprising the step of embedding a visible or invisible mark in the calibrated image, wherein the mark is configured to indicate whether the calibrated image has been calibrated such that one or more of the colors adjusted in the color calibrating step has an adjusted numeric color value that is within a defined margin of error from the corresponding known numeric color value.

15. The method of claim 14, further comprising the steps of: calculating a differential between the adjusted numeric color value and the defined margin of error, and embedding the differential in the calibrated image.

16. A method of calibrating an image of a patient's wound or skin condition, said method comprising the steps of: positioning a calibration slate in a location adjacent to a wound or skin condition on a patient, wherein the calibration slate has a print run number that identifies a batch of printed calibration slates which includes the calibration slate positioned in a location adjacent to the wound or skin condition on the patient, a unique identifier that individually identifies the calibration slate positioned in a location adjacent to the wound or skin condition on the patient, and a color chart comprising at least one color;

capturing an image that includes the wound or skin condition and the calibration slate using an image recording device;

reading the unique identifier and validating the calibration slate based on the unique identifier;

measuring a numeric color value from the at least one color in the color chart of the calibration slate as the calibration slate appears in the captured image;

reading the print run number;

associating the print run number with the batch of printed calibration slates which includes the calibration slate appearing in the captured image, wherein each calibration slate in the batch is substantially similar, wherein the measured numeric color value has a corresponding known numeric color value associated with the batch of calibration slates;

comparing the measured numeric color value to the corresponding known numeric color value;

calculating a variance between the measured numeric color value and the corresponding known numeric color value;

calculating a calibration factor based on the variance between the measured numeric color value and the corresponding known numeric color value; and color calibrating the captured image by adjusting the colors of the captured image to produce a calibrated image, wherein the colors of the captured image are adjusted by applying the calibration factor to numeric color values measured from the captured image.

17. The method of claim 16, wherein the unique identifier is machine-readable.

18. The method of claim 16, wherein the step of validating the calibration slate comprises verifying if the calibration slate was previously used for calibrating an image.

19. The method of claim 16, further comprising the step of determining the scale of objects relating to a subject and appearing in the captured image based on known measurements of one or more objects printed on the calibration slate appearing in the captured image.

20. The method of claim 16, further comprising the steps of:

consecutively capturing one or more additional images of a subject, wherein the subject is the same subject in each of the one or more additional captured images, wherein each of the one or more additional captured images includes a calibration slate appearing in each of the one or more additional captured images, respectively, independently color calibrating each of the one or more additional captured images to produce one or more additional calibrated images, and comparing each of the one or more additional calibrated images to the preceding calibrated image to determine how the subject has changed over time.

21. The method of claim 16, further comprising the steps of:

measuring a plurality of corresponding numeric color values directly from a plurality of respective calibration slates within the batch of printed calibration slates, and calculating the variance between the plurality of numeric color values measured from the plurality of respective calibration slates to verify that all slates within the batch are substantially similar.

22. The method of claim 16, further comprising the step of graphically attaching a second color chart to the captured image including the calibration slate, wherein the second color chart comprises a set of colors having known numeric color values, wherein each color in the set of colors on the second color chart is substantially similar to a respective corresponding color associated with the batch of calibration slates.

23. The method of claim 16, further comprising the step of attaching the calibration slate to a subject using an adhesive attached to the calibration slate before capturing the image that includes the calibration slate.

24. The method of claim 16, further comprising the step of associating the calibration slate appearing in the captured image with a patient based on patient identification information included on the calibration slate.

25. The method of claim 24, wherein the patient identification information is machine-readable, wherein the method further comprises the step of reading the patient identification information.

26. The method of claim 16, wherein the calibration slate appearing in the captured image further includes a focus chart comprising concentrically arranged shapes, wherein the focus chart is configured such that it can be used for grading the focus of the captured image, wherein the method further comprises the step of focusing the captured image using the focus chart before capturing the image.

27. The method of claim 16, further comprising the step of embedding a visible or invisible security mark in the captured image, wherein the security mark is configured to indicate whether the captured image has been altered.

28. The method of claim 16, further comprising the steps of: embedding a visible or invisible machine-readable unique number in the calibrated image that indicates that the calibrated image is certified, and certifying the calibrated image by reading the unique number.

29. The method of claim 16, further comprising the step of embedding a visible or invisible mark in the calibrated image, wherein the mark is configured to indicate whether the calibrated image has been calibrated such that one or more of the colors adjusted in the color calibrating step has an adjusted numeric color value that is within a defined margin of error from the corresponding known numeric color value.

30. The method of claim 29, further comprising the steps of: calculating a differential between the adjusted numeric color value and the defined margin of error, and embedding the differential in the calibrated image.

31. The method of claim 16, further comprising the step of embedding in the calibrated image: the measured numeric color value, the corresponding known numeric color value, the variance, the calibration factor, an adjusted numeric color value of one or more of the colors adjusted in the color calibrating step, or any combination thereof.

* * * * *